(12) United States Patent
Ahmed et al.

(10) Patent No.: US 11,883,191 B2
(45) Date of Patent: Jan. 30, 2024

(54) PNEUMONIA DETECTION IN CARDIOVASCULAR PATIENTS

(71) Applicant: Cardiac Pacemakers, Inc., St. Paul, MN (US)

(72) Inventors: Rezwan Ahmed, Arden Hills, MN (US); Qi An, Shoreview, MN (US); Viktoria A. Averina, Shoreview, MN (US); Pramodsingh Hirasingh Thakur, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 208 days.

(21) Appl. No.: 17/329,553

(22) Filed: May 25, 2021

(65) Prior Publication Data
US 2021/0369196 A1 Dec. 2, 2021

Related U.S. Application Data

(60) Provisional application No. 63/030,785, filed on May 27, 2020.

(51) Int. Cl.
| | |
|---|---|
| A61B 5/00 | (2006.01) |
| G16H 50/30 | (2018.01) |
| A61B 5/0205 | (2006.01) |
| A61B 5/08 | (2006.01) |
| A61B 5/091 | (2006.01) |
| A61B 5/11 | (2006.01) |
| A61B 7/04 | (2006.01) |

(52) U.S. Cl.
CPC .......... *A61B 5/4842* (2013.01); *A61B 5/0205* (2013.01); *A61B 5/7275* (2013.01); *A61B 5/7282* (2013.01); *G16H 50/30* (2018.01); *A61B 5/0816* (2013.01); *A61B 5/091* (2013.01); *A61B 5/1118* (2013.01); *A61B 7/04* (2013.01)

(58) Field of Classification Search
CPC ... A61B 5/4842; A61B 5/0205; A61B 5/7275; A61B 5/7282; A61B 5/0816; A61B 5/091; A61B 5/1118; A61B 7/04; G16H 50/30
USPC ........................................................ 600/301
See application file for complete search history.

(56) References Cited

U.S. PATENT DOCUMENTS

| | | |
|---|---|---|
| 7,115,096 B2 | 10/2006 | Siejko et al. |
| 7,575,553 B2 | 8/2009 | Stahmann et al. |

(Continued)

FOREIGN PATENT DOCUMENTS

| | | |
|---|---|---|
| CN | 115666381 A | 1/2023 |
| WO | WO-2021242723 A1 | 12/2021 |

OTHER PUBLICATIONS

"International Application Serial No. PCT/US2021/033989, International Preliminary Report on Patentability dated Dec. 8, 2022", 12 pgs.

(Continued)

*Primary Examiner* — Carl H Layno
*Assistant Examiner* — Michael J Lau
(74) *Attorney, Agent, or Firm* — Schwegman Lundberg & Woessner, P.A.

(57) ABSTRACT

Systems and methods to detect pneumonia in cardiovascular patients are disclosed, including receiving physiologic information of a patient from an ambulatory medical device (AMD), the physiologic information comprising respiration information of the patient, and determining a pneumonia score of the patient using the received respiration information.

20 Claims, 7 Drawing Sheets

(56) References Cited

U.S. PATENT DOCUMENTS

| | | |
|---|---|---|
| 7,678,061 B2 | 3/2010 | Lee et al. |
| 7,766,842 B2 | 8/2010 | Ni et al. |
| 9,345,410 B2 | 5/2016 | Thakur et al. |
| 9,968,266 B2 | 5/2018 | An et al. |
| 2014/0005502 A1* | 1/2014 | Klap ................ A61M 16/0057 600/300 |
| 2015/0148699 A1* | 5/2015 | Wariar ................ A61B 5/0809 600/533 |
| 2015/0250428 A1* | 9/2015 | Zhang .................... G16Z 99/00 600/300 |
| 2015/0327776 A1* | 11/2015 | Zhang .................... A61B 7/04 600/300 |
| 2018/0199888 A1* | 7/2018 | Varkey ................ A61B 5/7264 |
| 2019/0029601 A1* | 1/2019 | An ....................... A61B 5/0816 |
| 2019/0167205 A1 | 6/2019 | An et al. |
| 2019/0167209 A1 | 6/2019 | Annoni et al. |
| 2019/0209022 A1 | 7/2019 | Sobol et al. |
| 2020/0057050 A1* | 2/2020 | Wen .................... G01N 33/505 |

OTHER PUBLICATIONS

"International Application Serial No. PCT/US2021/033989, International Search Report dated Sep. 16, 2021", 7 pgs.

"International Application Serial No. PCT/US2021/033989, Written Opinion dated Sep. 16, 2021", 10 pgs.

\* cited by examiner

PNEUMONIA DETECTION IN CARDIOVASCULAR PATIENTS

CLAIM OF PRIORITY

This application claims the benefit of priority under 35 U.S.C. § 119(e) of U.S. Provisional Patent Application Ser. No. 63/030,785, filed on May 27, 2020, which is herein incorporated by reference in its entirety.

TECHNICAL FIELD

This document relates generally to detecting pneumonia, and more particularly, but not by way of limitation, to systems and methods for detecting pneumonia in cardiovascular patients.

BACKGROUND

Ambulatory medical devices (AMDs) include implantable, subcutaneous, wearable, external, or one or more other type of medical devices having sensors configured to sense physiologic signals from a patient. Detected physiologic signals can be used to determine or monitor patient status or condition, such as a cardiovascular status of the patient. Frequent patient monitoring, such as using one or more AMDs, can enable early detection of worsening patient condition or identification of patients or groups of patients having elevated risk of future adverse events, including hospitalization. Early detection of worsening patient condition can prevent or reduce patient hospitalization. Identifying and safely managing patient risk of worsening condition may reduce patient hospitalizations, the amount or severity of medical interventions, and overall healthcare costs.

SUMMARY

Systems and methods to detect pneumonia in cardiovascular patients are disclosed, including receiving physiologic information of a patient from an ambulatory medical device (AMD), such as a cardiac rhythm management device, and determining a pneumonia score of the patient using the received physiologic information. In an example, physiologic information of the patient can include one or more of respiration information of the patient, heart sound information of the patient, activity information of the patient, heart rate information of the patient, or combinations thereof.

In an example, the received physiologic information can include respiration information of the patient, including respiratory rate information and respiratory volume information of the patient. An assessment circuit can be configured to determine a rapid shallow breathing index (RSBI) value of the patient with respect to a first time period using the received respiration information, and to determine the pneumonia score of the patient using the determined RSBI value of the patient with respect to the first time period. The first time period can include a daily time period and the RSBI value for the patient with respect to the first time period can include a daily RSBI value for the patient. The assessment circuit can be configured to determine a change in the daily RSBI value for the patient over multiple days, and to determine the pneumonia score of the patient using the determined change in the daily RSBI value.

An example (e.g., "Example 1") of subject matter (e.g., a system) may comprise a signal receiver circuit configured to receive physiologic information of a patient from an ambulatory medical device (AMD), the physiologic information comprising respiration information of the patient, and an assessment circuit configured to determine a pneumonia score of the patient using the received respiration information.

In Example 2, the subject matter of Example 1 may optionally be configured such that the respiration information of the patient comprises respiratory rate information and respiratory volume information of the patient and the assessment circuit is configured to determine a rapid shallow breathing index (RSBI) value for the patient with respect to a first time period using the received respiration information, and to determine the pneumonia score of the patient using the determined RSBI value for the patient with respect to the first time period.

In Example 3, the subject matter of any one or more of Examples 1-2 may optionally be configured such that the first time period is a daily time period and the RSBI value for the patient with respect to the first time period comprises a daily RSBI value for the patient and the assessment circuit is configured to determine a change in the daily RSBI value for the patient over multiple days, and to determine the pneumonia score of the patient using the determined change in the daily RSBI value.

In Example 4, the subject matter of any one or more of Examples 1-3 may optionally be configured such that the physiologic information comprises heart rate information of the patient and the assessment circuit is configured to determine the pneumonia score of the patient using the received respiration information and the received heart rate information.

In Example 5, the subject matter of any one or more of Examples 1-4 may optionally be configured such that the physiologic information comprises respiration information of the patient, heart sound information of the patient, and activity information of the patient, the respiration information comprises respiratory rate information of the patient, the heart sound information comprises third heart sound (S3) information of the patient, the activity information comprises an indication of daily activity above an activity threshold of the patient, and the assessment circuit is configured to determine the pneumonia score of the patient using a combination of the received respiratory rate information of the patient, the received third heart sound (S3) information of the patient, and the received indication of daily activity above the activity threshold of the patient.

In Example 6, the subject matter of any one or more of Examples 1-5 may optionally be configured such that the physiologic information comprises temperature information of the patient, the assessment circuit is configured to determine the pneumonia score of the patient using the received respiration information and the received temperature information of the patient, and, to determine the pneumonia score of the patient, the assessment circuit is configured to determine at least one of an indication of worsening pneumonia status or a prediction of a future pneumonia event of the patient.

In Example 7, the subject matter of any one or more of Examples 1-6 may optionally be configured such that the physiologic information comprises respiration information of the patient, heart sound information of the patient, and activity information of the patient, and the assessment circuit is configured to detect an indication of worsening patient status using the received physiologic information of the patient, determine a heart failure score of the patient using a combination of the received respiration information of the patient, the received heart sound information of the patient, and the received activity information of the patient, and determine a diagnostic score indicative of a likelihood that the detected indication of worsening patient status is caused by heart failure or pneumonia using the determined pneumonia score and the determined heart failure score.

In Example 8, the subject matter of any one or more of Examples 1-7 may optionally be configured such that the diagnostic score indicative of the likelihood that the detected indication of worsening patient status is caused by heart failure or pneumonia comprises a first indication that the detected indication of worsening patient status is caused by heart failure and a second indication that the detected indication of worsening patient status is caused by pneumonia.

In Example 9, the subject matter of any one or more of Examples 1-8 may optionally comprise an external programmer configured to receive physiologic information from each of a group of patients, wherein the external programmer is configured to receive location information from each of the group of patients, and to determine geographic indicators of pneumonia related events of the group of patients using the received physiologic information and the receive location information.

In Example 10, the subject matter of any one or more of Examples 1-9 may optionally be configured such that the external programmer includes the assessment circuit, and the external programmer is configured to determine the geographic indicators of pneumonia related events of the group of patients using the determined pneumonia score and the received location information for each of the group of patients.

An example (e.g., "Example 11") of subject matter (e.g., a method) may comprise receiving, at a signal receiver circuit, physiologic information of a patient from an ambulatory medical device (AMD), the physiologic information comprising respiration information of the patient and determining, using an assessment circuit, a pneumonia score of the patient using the received respiration information.

In Example 12, the subject matter of Example 11 may optionally be configured such that the respiration information of the patient comprises respiratory rate information and respiratory volume information of the patient, the method optionally comprising determining, using the assessment circuit, a rapid shallow breathing index (RSBI) value for the patient with respect to a first time period using the received respiration information, wherein determining the pneumonia score of the patient comprises using the determined RSBI value for the patient with respect to the first time period.

In Example 13, the subject matter of any one or more of Examples 1-12 may optionally be configured such that the first time period is a daily time period and the RSBI value for the patient with respect to the first time period comprises a daily RSBI value for the patient, the method optionally comprising determining, using the assessment circuit, a change in the daily RSBI value for the patient over multiple days, wherein determining the pneumonia score of the patient comprises using the determined change in the daily RSBI value.

In Example 14, the subject matter of any one or more of Examples 1-13 may optionally be configured such that the physiologic information comprises heart rate information of the patient and determining the pneumonia score of the patient comprises using the received respiration information and the received heart rate information.

In Example 15, the subject matter of any one or more of Examples 1-14 may optionally be configured such that the physiologic information comprises respiration information of the patient, heart sound information of the patient, and activity information of the patient, the respiration information comprises respiratory rate information of the patient, the heart sound information comprises third heart sound (S3) information of the patient, the activity information comprises an indication of daily activity above an activity threshold of the patient, wherein determining the pneumonia score of the patient comprises using a combination of the received respiratory rate information of the patient, the received third heart sound (S3) information of the patient, and the received indication of daily activity above the activity threshold of the patient.

In Example 16, the subject matter of any one or more of Examples 1-15 may optionally be configured such that the physiologic information comprises respiration information of the patient, heart sound information of the patient, and activity information of the patient, the method optionally comprising detecting, using the assessment circuit, an indication of worsening patient status using the received physiologic information of the patient, determining, using the assessment circuit, a heart failure score of the patient using a combination of the received respiration information of the patient, the received heart sound information of the patient, and the received activity information of the patient, and determining, using the assessment circuit, a diagnostic score indicative of a likelihood that the detected indication of worsening patient status is caused by heart failure or pneumonia using the determined pneumonia score and the determined heart failure score.

In Example 17, the subject matter of any one or more of Examples 1-16 may optionally be configured such that determining the diagnostic score indicative of the likelihood that the detected indication of worsening patient status is caused by heart failure or pneumonia comprises determining a first indication that the detected indication of worsening patient status is caused by heart failure and determining a second indication that the detected indication of worsening patient status is caused by pneumonia.

In Example 18, the subject matter of any one or more of Examples 1-17 may optionally comprise receiving, using an external programmer, physiologic information from each of a group of patients and location information from each of the group of patients and determining, using the external programmer, geographic indicators of pneumonia related events of the group of patients using the received physiologic information and the receive location information.

An example (e.g., "Example 19") of subject matter (e.g., at least one machine-readable medium) may comprise instructions that, when performed by a medical device, cause the medical device to receive physiologic information of a patient from an ambulatory medical device (AMD), the physiologic information comprising respiration information of the patient and determine a pneumonia score of the patient using the received respiration information.

In Example 20, the subject matter of Example 19 may optionally be configured such that the instructions, when performed by the medical device, cause the medical device to determine a rapid shallow breathing index (RSBI) value for the patient with respect to a daily time period of the patient using the received respiration information, determine a change in the daily RSBI value for the patient over multiple days, wherein to determine the pneumonia score of the patient comprises using the determined change in the daily RSBI value.

In Example 21, subject matter (e.g., a system or apparatus) may optionally combine any portion or combination of any portion of any one or more of Examples 1-20 to comprise "means for" performing any portion of any one or more of the functions or methods of Examples 1-20, or at least one "non-transitory machine-readable medium" including instructions that, when performed by a machine, cause the machine to perform any portion of any one or more of the functions or methods of Examples 1-20.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
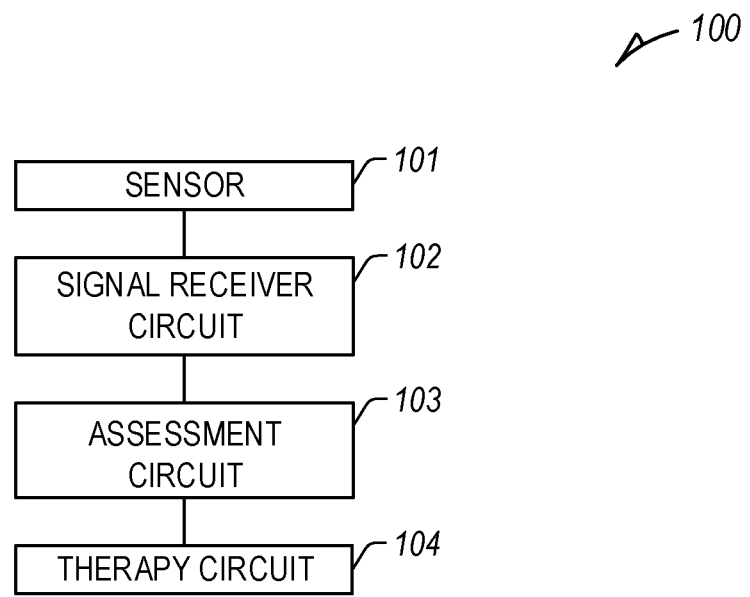
FIG. 1 illustrates an example system comprising a signal receiver circuit and an assessment circuit.

A large percentage of inpatients presenting with pneumonia or pneumonia-like symptoms suffer cardiac complications in contrast to outpatients presenting similar symptoms. For example, 27% of inpatient pneumonia treatment involves cardiac complications compared to just 2% of outpatient pneumonia treatment, with 66% of such cardiac complications for both inpatients and outpatients being new or worsening heart failure, with the remainder including new or worsening cardiac arrhythmias, myocardial infarction, etc.

Inpatient treatment for pneumonia often includes application of intravenous fluids. However, in patients with weak or compromised cardiovascular systems, introduction of additional fluids can exacerbate cardiac complications, including worsening heart failure.

Ambulatory medical devices (AMDs) are commonly used to monitor patients for new or worsening cardiac complications, including heart failure, arrhythmias, myocardial infarction, etc. The present inventors have recognized, among other things, systems and methods to monitor and determine a pneumonia status of a patient using existing cardiac rhythm management systems and sensors, adding diagnostic capabilities to existing systems and sensors, reducing potentially harmful patient intervention, and enabling early detection and treatment of patient pneumonia or respiratory distress with respect a patient cardiac status. In certain examples, such benefits can be accomplished without significant hardware changes to existing cardiac rhythm management devices. For example, physiologic information of the patient, such as patient respiration information (e.g., respiratory rate (RR), tidal volume (TV), rapid shallow breathing index (RSBI) (the ratio of respiratory frequency to tidal volume, e.g., RR/TV, etc.), etc.), or other physiologic information of the patient (e.g., heart rate (e.g., nighttime HR, etc.), etc.), in certain examples, already used to determine a cardiac status of the patient, can be used in a new capacity, such as to determine a pneumonia score of the patient. The pneumonia score of the patient can indicate, in various examples, a current pneumonia status or worsening pneumonia status of the patient or a prediction of a future pneumonia event, such as using previous pneumonia event information of the patient or one or more other patients or patient populations. The prediction of the future pneumonia event can include a prediction of a most likely time of a future pneumonia event or a likelihood of a future pneumonia event occurring within a future time period (e.g., over the next week, two weeks, one month, etc.).

Immunocompromised patients, or patients with cardiac complications, including patients already having implantable or ambulatory cardiac rhythm management devices are already at a higher risk of infections viruses, transmittable diseases, etc. Enabling additional sensing capabilities of existing devices and sensor combinations, such as with software updates remotely using a medical device programmer, improves existing cardiac rhythm management devices and methods.

FIG. 1 illustrates an example system 100, such as a medical-device system, etc. In an example, one or more aspects of the example system 100 can be a component of, or communicatively coupled to, one or more AMDs. AMDs can be configured to monitor, detect, or treat various physiologic conditions of the body, such as cardiac conditions associated with a reduced ability of a heart to sufficiently deliver blood to a body, including HF, arrhythmias, hypertension, dyssynchrony, etc. AMDs can include a single device or a plurality of medical devices or monitors implanted in a patient's body or otherwise positioned on or about the patient to monitor patient physiologic information of the patient, such as using one or more sensors, the physiologic information including one or more of heart sounds, respiration (e.g., respiratory rate (RR), tidal volume (TV), etc.), impedance (e.g., thoracic impedance, cardiac impedance, cutaneous impedance, etc.), pressure (e.g., blood pressure), cardiac activity (e.g., heart rate, cardiac electrical information, etc.), chemical (e.g., electrolyte), physical activity, posture, plethysmography, or one or more other physiologic parameters of a patient, or to provide electrical stimulation or one or more other therapies or treatments to the patient.

The example system 100 can include a signal receiver circuit 102 and an assessment circuit 103. The signal receiver circuit 102 can be configured to receive physiologic information of a patient (or group of patients) from one or more sensors 101. The assessment circuit 103 can be configured to receive information from the signal receiver circuit 102, and to determine one or more parameters (e.g., physiologic parameters, stratifiers, etc.) or existing or changed patient conditions (e.g., indications of patient hydration or dehydration, respiratory condition (e.g. COPD, asthma), pneumonia status, cardiac condition (e.g. heart failure, arrhythmia), etc.) using the received physiologic information of the patient (or group of patients), such as described herein. The physiologic information of the patient (or group of patients) can include, among other things, absolute or relative measures or changes in cardiac electrical information, impedance information, respiration information, heart sound information, activity information, posture information, temperature information, chemical information, etc.

In an example, the sensor 101 can include one or more of: a respiration sensor configured to receive respiration information (e.g., a respiratory rate, a respiration volume (tidal volume), etc.); an acceleration sensor (e.g., an accelerometer, a microphone, etc.) configured to receive cardiac acceleration information (e.g., cardiac vibration information, pressure waveform information, heart sound information, endocardial acceleration information, acceleration information, activity information, posture information, etc.); an impedance sensor (e.g., intrathoracic impedance sensor, transthoracic impedance sensor, etc.) configured to receive impedance information, a cardiac sensor configured to receive cardiac electrical information; an activity sensor configured to receive information about a physical motion (e.g., activity, steps, etc.); a posture sensor configured to receive posture or position information; a pressure sensor configured to receive pressure information; a plethysmograph sensor (e.g., a photoplethysmography sensor, etc.); a chemical sensor (e.g., an electrolyte sensor, a pH sensor, an anion gap sensor, etc.); a skin temperature sensor (e.g., absolute or relative change in temperature, indicating an increase in patient core temperature, etc.); a skin elasticity sensor, or one or more other sensors configured to receive physiologic information of the patient.

The assessment circuit 103 can be configured to provide an output to a user, such as to a display or one or more other user interface, the output including a score, a trend, an alert, or other indication. In other examples, the assessment circuit 103 can be configured to provide an output to another circuit, machine, or process, such as a therapy circuit 104 (e.g., a cardiac resynchronization therapy (CRT) circuit, a chemical therapy circuit, etc.), etc., to control, adjust, or cease a therapy of a medical device, a drug delivery system, etc., or otherwise alter one or more processes or functions of one or more other aspects of a medical-device system, such as one or more CRT parameters, drug delivery, dosage determinations or recommendations, etc. In an example, the therapy circuit 104 can include one or more of a stimulation control circuit, a cardiac stimulation circuit, a neural stimulation circuit, a dosage determination or control circuit, etc. In other examples, the therapy circuit 104 can be controlled by the assessment circuit 103, or one or more other circuits, etc.

In an example, a single AMD can include each of the sensor 101, the signal receiver circuit 102, the assessment circuit 103, and the therapy circuit 104 can be included in a single AMD. In other examples, an AMD can include one or more of the sensor 101, the signal receiver circuit 102, the assessment circuit 103, or the therapy circuit 104, in combination with other medical devices (e.g., one or more other AMDs, external devices, remote devices, medical devices, medical device programmers, etc.).

AMDs can include a range of medical devices, including, for example, traditional cardiac rhythm management (CRM) devices, such as pacemakers, defibrillators, or cardiac resynchronizers, include implantable or subcutaneous devices configured to be implanted in a chest of a patient. The CRM device can include one or more leads to position one or more electrodes or other sensors at various locations in or near the heart, such as in one or more of the atria or ventricles. Separate from, or in addition to, the one or more electrodes or other sensors of the leads, the CRM device can include one or more electrodes or other sensors (e.g., a pressure sensor, an accelerometer, a gyroscope, a microphone, etc.) powered by a power source in the CRM device. The one or more electrodes or other sensors of the leads, the CRM device, or a combination thereof, can be configured detect physiologic information from the patient, or provide one or more therapies or stimulation to the patient.

Implantable devices can additionally or separately include leadless cardiac pacemakers (LCP), small (e.g., smaller than traditional implantable CRM devices, in certain examples having a volume of about 1 cc, etc.), self-contained devices including one or more sensors, circuits, or electrodes configured to monitor physiologic information (e.g., heart rate, etc.) from, detect physiologic conditions (e.g., tachycardia) associated with, or provide one or more therapies or stimulation to the heart without traditional lead or implantable CRM device complications (e.g., required incision and pocket, complications associated with lead placement, breakage, or migration, etc.). In certain examples, an LCP can have more limited power and processing capabilities than a traditional CRM device; however, multiple LCP devices can be implanted in or about the heart to detect physiologic information from, or provide one or more therapies or stimulation to, one or more chambers of the heart. The multiple LCP devices can communicate between themselves, or one or more other implanted or external devices.

Each additional sensor within or associated with an AMD or medical device system can increase system cost and complexity, reduce system reliability, or increase the power consumption and reduce the usable life of the AMD. Accordingly, it can be beneficial to use a single sensor to determine multiple types of physiologic information, or a smaller number of sensors to measure a larger number of different types of physiologic information. For example, it can be beneficial to detect atrial cardiac electrical information without a lead or an electrode in, or in contact with, the atria. Similarly, it can be beneficial to detect or predict new or additional patient status indications using existing sensors and devices.

Figure 2:
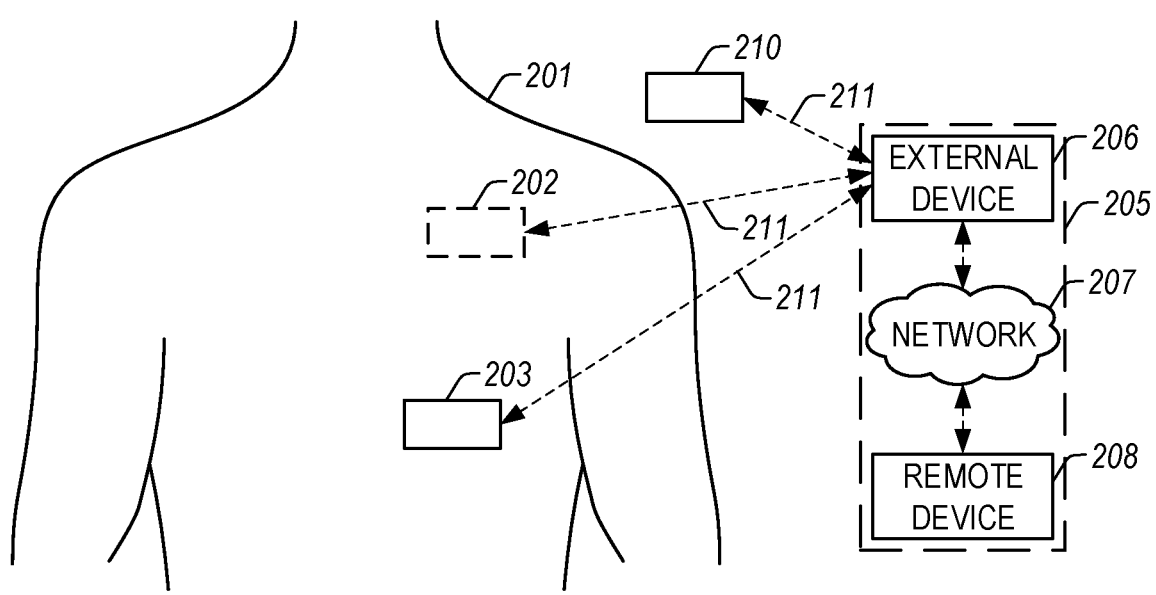
FIG. 2 illustrates an example patient management system.

FIG. 2 illustrates an example patient management system 200 and portions of an environment in which the system 200 may operate. The patient management system 200 can perform a range of activities, including remote patient monitoring and diagnosis of a disease condition. Such activities can be performed proximal to a patient 201, such as in a patient home or office, through a centralized server, such as in a hospital, clinic, or physician office, or through a remote workstation, such as a secure wireless mobile computing device.

The patient management system 200 can include one or more AMDs, an external system 205, and a communication link 211 providing for communication between the one or more AMDs and the external system 205. The one or more AMDs can include an implantable medical device (IMD) 202, a wearable medical device 203, or one or more other implantable, leadless, subcutaneous, external, wearable, or AMDs configured to monitor, sense, or detect information from, determine physiologic information about, or provide one or more therapies to treat various conditions of the patient 201, such as one or more cardiac or non-cardiac conditions (e.g., dehydration, etc.).

In an example, the IMD 202 can include one or more traditional cardiac rhythm management (CRM) devices, such as a pacemaker or defibrillator, implanted in a chest of a patient, having a lead system including one or more transvenous, subcutaneous, or non-invasive leads or catheters to position one or more electrodes or other sensors (e.g., a heart sound sensor) in, on, or about a heart or one or more other position in a thorax, abdomen, or neck of the patient 201. In another example, the IMD 202 can include a monitor implanted, for example, subcutaneously in the chest of patient 201.

The IMD 202 can include an assessment circuit configured to detect or determine specific physiologic information of the patient 201, or to determine one or more conditions or provide information or an alert to a user, such as the patient 201 (e.g., a patient), a clinician, or one or more other caregivers or processes. The IMD 202 can alternatively or additionally be configured as a therapeutic device configured to treat one or more medical conditions of the patient 201. The therapy can be delivered to the patient 201 via the lead system and associated electrodes or using one or more other delivery mechanisms. The therapy can include delivery of one or more drugs to the patient 201 using the IMD 202 or one or more of the other AMDs. In some examples, therapy can include CRT for rectifying dyssynchrony and improving cardiac function in CHF patients. In other examples, the IMD 202 can include a drug delivery system, such as a drug infusion pump to deliver drugs to the patient for managing arrhythmias or complications from arrhythmias, hypertension, or one or more other physiologic conditions.

The wearable medical device 203 can include one or more wearable or external medical sensors or devices (e.g., automatic external defibrillators (AEDs), Holter monitors, patch-based devices, smart watches, smart accessories, wrist- or finger-worn medical devices, such as a finger-based photoplethysmography sensor, etc.). The wearable medical device 203 can include an optical sensor configured to detect a PPG signal on a wrist, finger, or other location on the patient 201. In other examples, the wearable medical device 203 can include an acoustic sensor or accelerometer to detect acoustic information (e.g., heart sounds) or the sound or vibration of blood flow, an impedance sensor to detect impedance variations associated with changes in blood flow or volume, a temperature sensor to detect temperature variation associated with blood flow, a laser Doppler vibrometer or other pressure, strain, or physical sensor to detect physical variations associated with blood flow, etc.

The patient management system 200 can include, among other things, a respiration sensor configured to receive respiration information (e.g., respiratory rate (RR), respiration volume (a minute volume (MV), a tidal volume (TV), etc.), etc.), a heart sound sensor configured to receive heart sound information, a thoracic impedance sensor configured to receive impedance information, a cardiac sensor configured to receive cardiac electrical information, an activity sensor configured to receive information about a physical motion (e.g., activity, posture, etc.), a plethysmography sensor, or one or more other sensors configured to receive physiologic information of the patient 201.

The external system 205 can include a dedicated hardware/software system, such as a programmer, a remote server-based patient management system, or alternatively a system defined predominantly by software running on a standard personal computer. The external system 205 can manage the patient 201 through the IMD 202 or one or more other AMDs connected to the external system 205 via a communication link 211. In other examples, the IMD 202 can be connected to the wearable device 203, or the wearable device 203 can be connected to the external system 205, via the communication link 211. This can include, for example, programming the IMD 202 to perform one or more of acquiring physiologic data, performing at least one self-diagnostic test (such as for a device operational status), analyzing the physiologic data to detect a cardiac arrhythmia, or optionally delivering or adjusting a therapy to the patient 201. Additionally, the external system 205 can send information to, or receive information from, the IMD 202 or the wearable device 203 via the communication link 211. Examples of the information can include real-time or stored physiologic data from the patient 201, diagnostic data, such as detection of patient hydration status, hospitalizations, responses to therapies delivered to the patient 201, or device operational status of the IMD 202 or the wearable device 203 (e.g., battery status, lead impedance, etc.). The communication link 211 can be an inductive telemetry link, a capacitive telemetry link, or a radio-frequency (RF) telemetry link, or wireless telemetry based on, for example, "strong" Bluetooth or IEEE 802.11 wireless fidelity "Wi-Fi" interfacing standards. Other configurations and combinations of patient data source interfacing are possible.

By way of example and not limitation, the external system 205 can include an external device 206 in proximity of the one or more AMDs, and a remote device 208 in a location relatively distant from the one or more AMDs, in communication with the external device 206 via a communication network 207. Examples of the external device 206 can include a medical device programmer.

The remote device 208 can be configured to evaluate collected patient or patient information and provide alert notifications, among other possible functions. In an example, the remote device 208 can include a centralized server acting as a central hub for collected data storage and analysis. The server can be configured as a uni- multi- or distributed computing and processing system. The remote device 208 can receive data from multiple patients. The data can be collected by the one or more AMDs, among other data acquisition sensors or devices associated with the patient 201. The server can include a memory device to store the data in a patient database. The server can include an alert analyzer circuit to evaluate the collected data to determine if specific alert condition is satisfied. Satisfaction of the alert condition may trigger a generation of alert notifications, such to be provided by one or more human-perceptible user interfaces. In some examples, the alert conditions may alternatively or additionally be evaluated by the one or more AMDs, such as the IMD. By way of example, alert notifications can include a Web page update, phone or pager call, E-mail, SMS, text or "Instant" message, as well as a message to the patient and a simultaneous direct notification to emergency services and to the clinician. Other alert notifications are possible. The server can include an alert prioritizer circuit configured to prioritize the alert notifications. For example, an alert of a detected medical event can be prioritized using a similarity metric between the physiologic data associated with the detected medical event to physiologic data associated with the historical alerts.

The remote device 208 may additionally include one or more locally configured clients or remote clients securely connected over the communication network 207 to the server. Examples of the clients can include personal desktops, notebook computers, mobile devices, or other computing devices. System users, such as clinicians or other qualified medical specialists, may use the clients to securely access stored patient data assembled in the database in the server, and to select and prioritize patients and alerts for health care provisioning. In addition to generating alert notifications, the remote device 208, including the server and the interconnected clients, may also execute a follow-up scheme by sending follow-up requests to the one or more AMDs, or by sending a message or other communication to the patient 201 (e.g., the patient), clinician or authorized third party as a compliance notification.

The communication network 207 can provide wired or wireless interconnectivity. In an example, the communication network 207 can be based on the Transmission Control Protocol/Internet Protocol (TCP/IP) network communication specification, although other types or combinations of networking implementations are possible. Similarly, other network topologies and arrangements are possible.

One or more of the external device 206 or the remote device 208 can output the detected medical events to a system user, such as the patient or a clinician, or to a process including, for example, an instance of a computer program executable in a microprocessor. In an example, the process can include an automated generation of recommendations for anti-arrhythmic therapy, or a recommendation for further diagnostic test or treatment. In an example, the external device 206 or the remote device 208 can include a respective display unit for displaying the physiologic or functional signals, or alerts, alarms, emergency calls, or other forms of warnings to signal the detection of arrhythmias. In some examples, the external system 205 can include an external data processor configured to analyze the physiologic or functional signals received by the one or more AMDs, and to confirm or reject the detection of arrhythmias. Computationally intensive algorithms, such as machine-learning algorithms, can be implemented in the external data processor to process the data retrospectively to detect cardia arrhythmias.

Portions of the one or more AMDs or the external system 205 can be implemented using hardware, software, firmware, or combinations thereof. Portions of the one or more AMDs or the external system 205 can be implemented using an application-specific circuit that can be constructed or configured to perform one or more functions or can be implemented using a general-purpose circuit that can be programmed or otherwise configured to perform one or more functions. Such a general-purpose circuit can include a microprocessor or a portion thereof, a microcontroller or a portion thereof, or a programmable logic circuit, a memory circuit, a network interface, and various components for interconnecting these components. For example, a "comparator" can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals. "Sensors" can include electronic circuits configured to receive information and provide an electronic output representative of such received information.

The patient management system 200 can include a therapy device 210, such as a respiratory therapy device (e.g. continuous positive airway pressure device or nebulizer device, etc.) or a drug delivery device configured to provide therapy or therapy information (e.g., dosage information, etc.) to the patient 201, such as using information from one or more of the AMDs. In other examples, one or more of the AMDs can be configured to provide therapy or therapy information to the patient 201. The therapy device 210 can be configured to send information to or receive information from one or more of the AMDs or the external system 205 using the communication link 211. In an example, the one or more AMDs, the external device 206, or the remote device 208 can be configured to control one or more parameters of the therapy device 210.

The external system 205 can allow for programming the one or more AMDs and can receives information about one or more signals acquired by the one or more AMDs, such as can be received via a communication link 211. The external system 205 can include a local external IMD programmer. The external system 205 can include a remote patient management system that can monitor patient status or adjust one or more therapies such as from a remote location.

The assessment circuit may be implemented at the external system 205, which can be configured to perform HF risk stratification such as using data extracted from the one or more AMDs or data stored in a memory within the external system 205. Portions of patient chronic condition-based HF or other assessment circuit may be distributed between the one or more AMDs and the external system 205.

Figure 3:
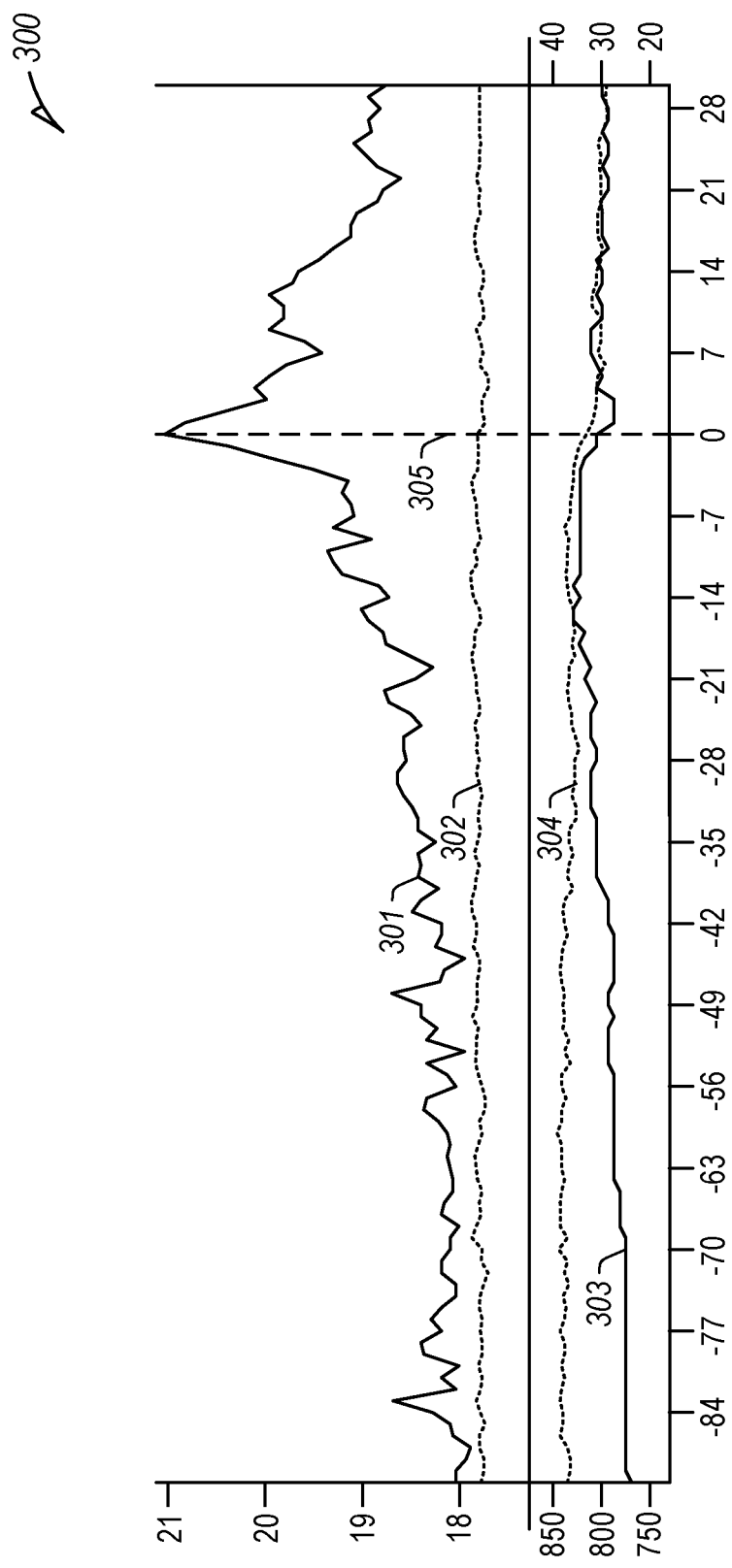
FIGS. 3-5 illustrate example patient physiologic information incident to hospitalization with pneumonia or pneumonia related events.
Figure 4:
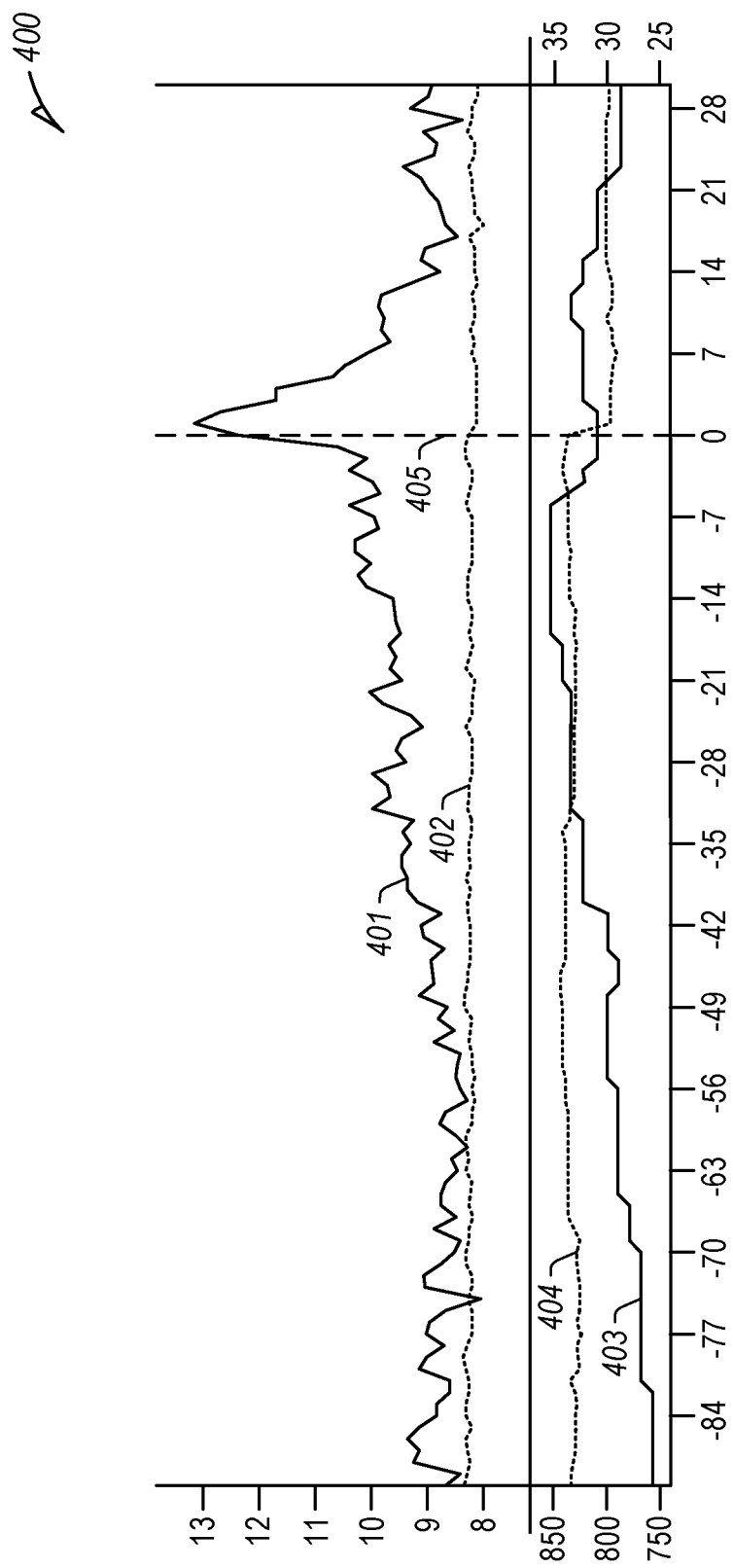
Figure 5:
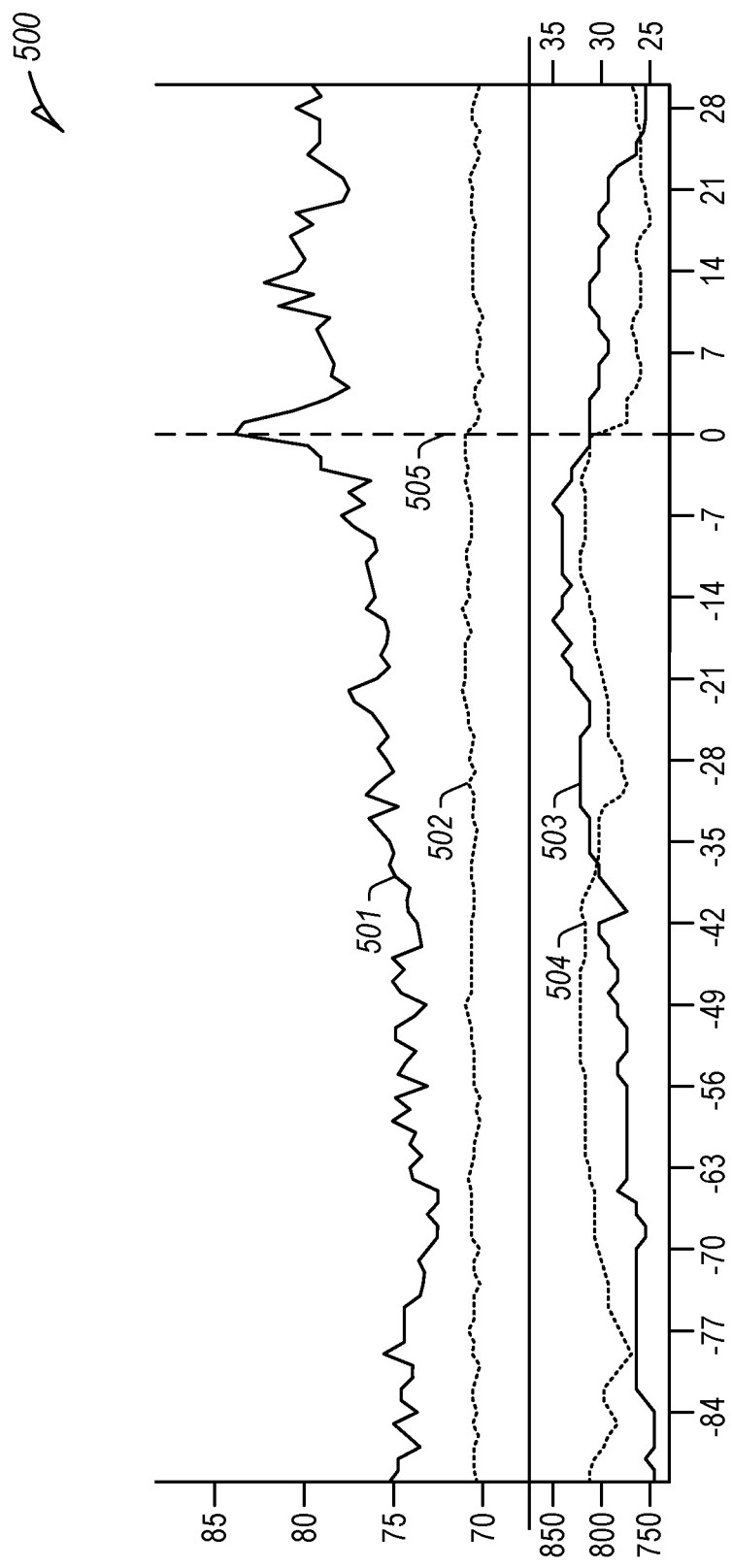

FIGS. 3-5 illustrate example relationships 300, 400, and 500 of patient physiologic information incident to hospitalization with a pneumonia related event, such as hospitalization of cardiovascular patient with a diagnosis of pneumonia. In certain examples, the physiologic information can include one or more of respiratory rate information, respiratory volume information, rapid shallow breathing index (RSBI) information, heart rate information, activity information, heart sound information, temperature information, etc. For example, one or more relationships between physiologic information and a pneumonia event can be determined, enabling one or more AMDs associated with one or more patients, or one or more programmers or external medical devices coupled to or configured to receive information from the one or more AMDs, to be able to detect or determine a pneumonia or worsening pneumonia status, or to predict a future pneumonia event in the one or more patients.

FIG. 3 illustrates example relationship 300 of daily respiratory rate information (e.g., breaths per minute) of a group of patients having implantable CRM devices configured to sense patient respiration information, the daily respiratory rate information plotted relative to an adverse pneumonia event 305 at day zero (0) on the horizontal axis. The daily respiratory rate information includes first daily respiratory rate information 301 of a sub-group of patients experiencing the adverse pneumonia event, and second daily respiratory rate information 302 of a sub-group of patients not experiencing an adverse pneumonia event. The first daily respiratory rate information 301 increases substantially in the days and weeks prior to the adverse pneumonia event 305, whereas the second daily respiratory rate information 302 remains substantially constant.

The daily respiratory rate information can include an average daily respiratory rate, a median respiratory rate, a minimum daily respiratory rate, a daily maximum respiratory rate, an upper or lower percentage of daily respiratory rate information (e.g., an upper or lower quartile, etc.), or one or more other measures of daytime (wake time, different than daily) or nighttime (or sleep time) respiratory rate information.

The example relationship 300 further includes a first number of patients 303 corresponding to the first daily respiratory rate information 301 with respect to the scale at right, and a second number of patients 304 corresponding to the second daily respiratory rate information 302 with respect to the scale at left.

FIG. 4 illustrates example relationship 400 of daily rapid shallow breathing index (RSBI) information (e.g., a ratio of respiratory rate (RR) to tidal volume (TV), etc.) of a group of patients having implantable CRM devices configured to sense patient respiration information, the daily RSBI information plotted relative to an adverse pneumonia event 405 at day zero (0) on the horizontal axis. The daily RSBI information includes first daily RSBI information 401 of a sub-group of patients experiencing the adverse pneumonia event, and second daily RSBI information 402 of a sub-group of patients not experiencing an adverse pneumonia event. The first daily RSBI information 401 increases substantially in the days and weeks prior to the adverse pneumonia event 405, whereas the second daily RSBI information 402 remains substantially constant.

The daily RSBI information can include an average daily RSBI, a median daily RSBI, a minimum daily RSBI, a daily maximum RSBI, an upper or lower percentage of daily RSBI information (e.g., an upper or lower quartile, etc.), or one or more other measures of daytime (wake time, different than daily) or nighttime (or sleep time) RSBI information.

The example relationship 400 further includes a first number of patients 403 corresponding to the first daily RSBI information 401 with respect to the scale at right, and a second number of patients 404 corresponding to the second daily RSBI information 402 with respect to the scale at left.

FIG. 5 illustrates example relationship 400 of daily heart rate information (e.g., a daily nighttime heart rate, etc.) of a group of patients having implantable CRM devices configured to sense patient electrical or mechanical information, the daily heart rate information plotted relative to an adverse pneumonia event 505 at day zero (0) on the horizontal axis. The daily heart rate information includes first daily heart rate information 501 of a sub-group of patients experiencing the adverse pneumonia event, and second daily heart rate information 502 of a sub-group of patients not experiencing an adverse pneumonia event. The first daily heart rate information 501 increases substantially in the days and weeks prior to the adverse pneumonia event 505, whereas the second daily heart rate information 502 remains substantially constant.

The daily heart rate information can include an average daily heart rate, a median daily heart rate, a minimum daily heart rate, a daily maximum heart rate, an upper or lower percentage of daily heart rate information (e.g., an upper or lower quartile, etc.), or one or more other measures of daytime (different than daily) or nighttime (or sleeping) heart rate information.

The example relationship 500 further includes a first number of patients 503 corresponding to the first daily heart rate information 501 with respect to the scale at right, and a second number of patients 504 corresponding to the second daily heart rate information 502 with respect to the scale at left.

Figure 6:
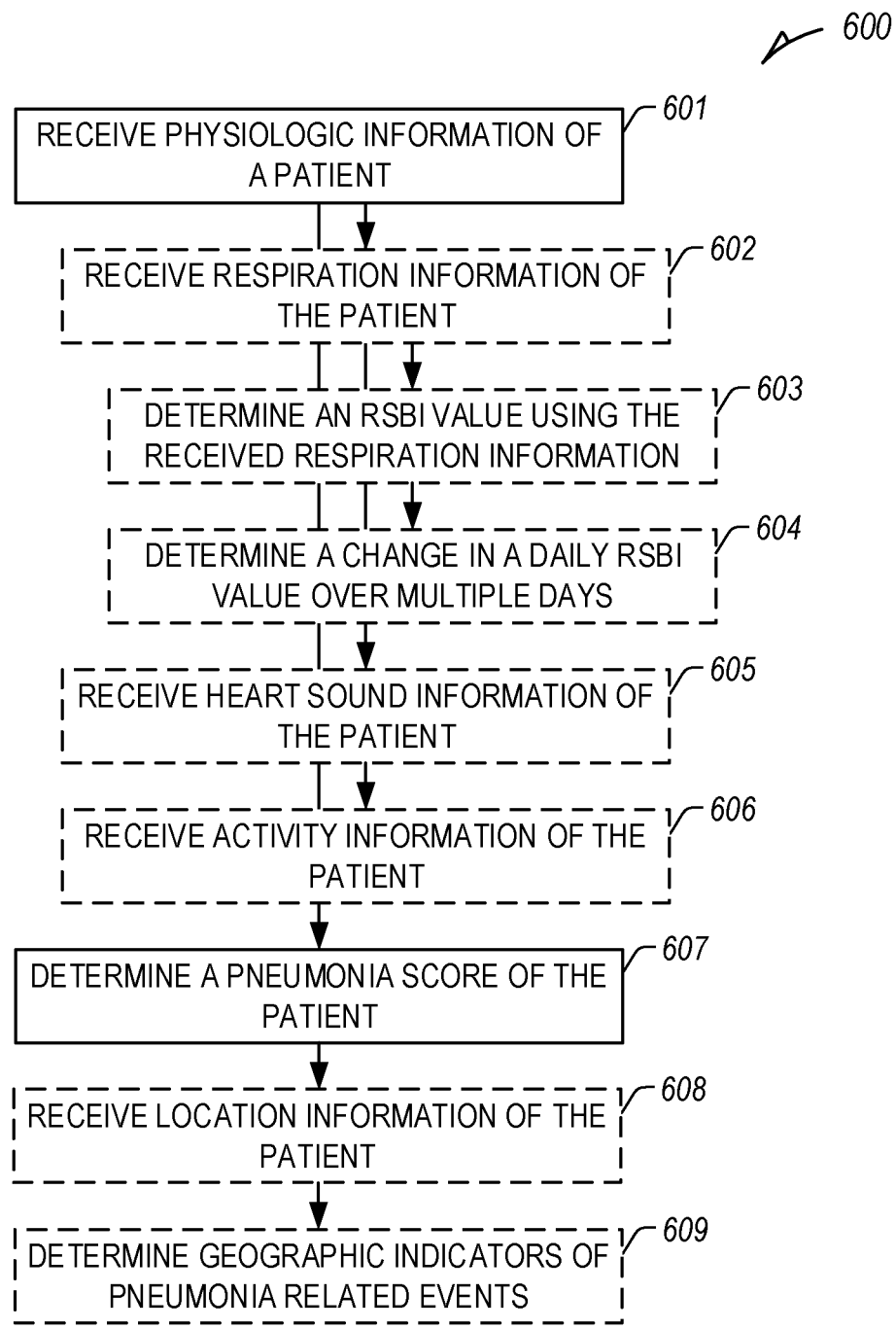
FIG. 6 illustrates an example method to determine a pneumonia score of a patient.

FIG. 6 illustrates an example method 600 to determine a pneumonia score of a patient using received physiological information, such as respiration information, cardiac electrical information, heart sound information, activity information, or other physiological information of the patient.

At 601, physiologic information can be received from the patient, such as using a signal receiver circuit of an ambulatory medical device, a medical device programmer, or one or more other implantable, external, ambulatory, or remote medical devices, such as disclosed herein.

At 602, the physiologic information received from the patient can optionally include respiration information of the patient. Respiration information can include a physiologic signal that varies with patient breathing or otherwise cyclical with patient respiration. In an example, the signal receiver circuit can be configured to receive respiratory rate (RR), tidal volume (TV), rapid shallow breathing index (RSBI), or one or more other respiratory measurements or parameters of the patient. In other examples, one or more assessment circuits can be configured to determine one or more respiratory parameters, such as those described above, using the received patient respiration information.

At 603, the RSBI value for the patient can be determined using the received patient respiration, such as by the assessment circuit. The RSBI value can be determined as a ratio of respiratory frequency to tidal volume (e.g., RR/TV, etc.). In an example, different respiratory parameters or metrics can be determined corresponding to different time periods, such as daily time periods, or time periods associated with one or more other time periods (e.g., hours, days, weeks, etc.). For example, respiration metrics can include an average, median, maximum, or minimum respiratory rate over a specific time period, such as a day, etc. In certain examples, such metrics can be further limited to daytime or nighttime measurements, confirmed using a detected or received indication of patient sleep or wake status, by a clock, activity, posture, etc.

In an example, the RSBI value can include a daily RSBI value determined as a daily respiratory rate value (e.g., an average daily respiratory rate, a median daily respiratory rate, a minimum daily respiratory rate, a maximum daily respiratory rate, etc.) divided by a daily tidal volume value (e.g., an average daily tidal volume, a median daily tidal volume, a minimum daily tidal volume, a maximum daily tidal volume, etc.). For example, the daily RSBI value can include a daily minimum RSBI value during daytime, or waking hours. In other examples, an RSBI value for a patient can be determined a number of times per day, and the daily RSBI value can be an average, median, minimum, maximum, or one or more other statistical values of the number of determined RSBI values for the day. In other examples, one or more other time periods longer than or shorter than a day can be used, such as a number of days (e.g., 3 days, etc.), a week, a month, etc., or a subset of a day (e.g., a daytime value, a nighttime value, etc.) for the daily or other time period. For example, the At 604, a change in daily RSBI value can be determined over a time period, such as a change within a day, the difference in the amount of change in successive days, or one or more other changes in a statistical measure (e.g., average, median, minimum, or maximum value, etc.) over multiple days.

At 605, the physiologic information received from the patient can optionally include heart sound information of the patient. Heart sounds are recurring mechanical signals associated with cardiac vibrations or accelerations from blood flow through the heart or other cardiac movements with each cardiac cycle and can be separated and classified according to activity associated with such vibrations, accelerations, movements, pressure waves, or blood flow. Heart sounds include four major features: the first through the fourth heart sounds. The first heart sound (S1) is the vibrational sound made by the heart during closure of the atrioventricular (AV) valves, the mitral valve and the tricuspid valve, at the beginning of systole. The second heart sound (S2) is the vibrational sound made by the heart during closure of the aortic and pulmonary valves at the beginning of diastole. The third and fourth heart sounds (S3, S4) are related to filling pressures of the left ventricle during diastole. Valve closures and blood movement and pressure changes in the heart can cause accelerations, vibrations, or movement of the cardiac walls that can be detected using an accelerometer or a microphone, providing an output referred to herein as cardiac acceleration information.

In an example, third heart sound (S3) information can be received or determined, such as daily S3 information, including an S3 amplitude or an amount of energy measured in an S3 window, etc. In other examples, first heart sound (S1) information can be received or determined, such as daily S1 information, including an S1 amplitude, etc. In other examples, one or more other heart sound information can be received or determined, such as one or more of S1 information, second heart sound (S2) information, S3 information, or fourth heart sound (S4) information. In certain examples, a ratio of different heart sound information can be received or determined, such as a ration of S3 information to S1 information, e.g., a daily S3/S1 measurement, etc.

Heart sounds can be used to detect or improve detection of a number of physiologic conditions, including, for example, acute physiologic events, such as one or more abnormal cardiac rhythms (e.g., atrial fibrillation, atrial flutter, cardiac mechanical dyssynchrony, etc.), or chronic physiologic events (e.g., ischemia, heart failure, etc.). For example, heart failure can be detected using heart sounds. For example, an index of third heart sound (S3) information can be used to monitor heart failure, such as disclosed in the commonly assigned Siejko et al. U.S. Pat. No. 7,115,096, titled "Third Heart Sound Activity Index for Heart Failure Monitoring", herein incorporated by reference in its entirety. A HF risk score can be determined, and WHF detection can be adjusted using a measured physiological parameter of a sensed S3 heart sound, such as disclosed in the commonly assigned An et al. U.S. Pat. No. 9,968,266, titled "Risk Stratification Based Heart Failure Detection Algorithm", herein incorporated by reference in its entirety. A physiologic indicator, such as a HF status indication, can be determined using a trend of a determined heart sound characteristic following a transition from an elevated activity level to a less elevated activity level, such as disclosed in the commonly assigned Thakur et al. U.S. Pat. No. 9,345,410, titled "Diagnostic and Optimization using Exercise Recovery Data", herein incorporated by reference in its entirety.

At 606, the physiologic information received from the patient can optionally include activity information of the patient, such as a daily amount of time (or count of time windows) having sustained, average, or maximum activity measurements above a specific activity threshold (e.g., representative of moderate activity, etc.). For example, the activity information can include a daily measure representative of a count of daily hours having activity measurements (or a percentage of activity measurements) above a moderate activity threshold (e.g., accelerometer measurements above 28 mg, etc.).

At 607, a pneumonia score of the patient can be determined using the received or determined physiological information, such as using the assessment circuit, etc. In an example, the pneumonia score can be determined using a relationship comprising one or more of the types of physiologic information. For example, the pneumonia score can be determined using a measure of patient respiration information, such as a received or determined RSBI value, etc. In other examples, the pneumonia score can be determined using one or more other types of received or determined physiologic information, such as heart rate information, heart sound information, activity information, or one or more other measures of respiration information, such as a trend of daily respiration rate, etc.

In certain examples, the pneumonia score can be determined using a number of combined measures of received or determined physiologic information. For example, the pneumonia score can be determined using a combination of at least two received or determined measures of different types of physiologic information, such as a respiration information, heart rate information, heart sound information, activity information, etc.

An example relationship to determine a pneumonia score (Ps) of a patient includes: $Ps=RSBI*a+RRT*b+Activity*c+HR*d$, where RSBI, RRT, Activity, and HR are respective measures of physiologic information, and a, b, c, and d are coefficients representing weights for respective measures. In other examples, other measures or mathematical combinations of measures or relationships can be used to determine the pneumonia score of the patient. In an example, the relationship to determine the pneumonia score can be determined using statistical analysis (e.g., machine learning techniques, such as linear models (e.g., Lasso & Ridge), tree based models (e.g., XG Boost, Cat Boost, Light GBM, random forest (RF), Decision Tree, etc.), etc.) of physiologic information, such as using the example relationships 300-500 illustrated in FIGS. 3-5.

Respective measures can include, among others, one or more of: a measure (e.g., a change) of daily average RSBI value, a measure in daily minimum daytime RSBI value, a measure of daily average respiratory rate, a measure of daily activity level above a threshold, a measure of daily nighttime heart rate, a measure of a daily heart sound value (e.g., an S3 amplitude or an amount of energy measured in an S3 window, etc.), or combinations of multiple measures, such as a combination of the measure of daily average respiratory rate, the measure of daily activity level above a threshold, and a measure of a daily S3 value. In other examples, respective measures can include index values (e.g., indexed from 0 to 20 with respect to a threshold, such as a population threshold, etc.) of one or more of the measures described above.

In other examples, the pneumonia score can be determined in response to one or more measures exceeding one or more thresholds. In certain examples, measures can be combined and compared to a single threshold, or individual measures or combinations of measures can be compared to respective thresholds.

At 608, location information can be received of the patient using the assessment circuit, or of a group of patients including the patient using the assessment circuit or one or more other medical devices, such as an external programmer, etc. Location information can include different levels of granularity, ranging from residence information of the patient or location of a medical care facility from medical records to a physical location information of the patient determined using at least one of a global positioning system (GPS), radio frequency identification (RFID), Bluetooth®, Wi-Fi®, near-field communication (NFC), cellular network, or paging network location information, etc.

At 609, geographic indicators of pneumonia or pneumonia related events, such as a viral, bacterial, or other disease outbreak, can be determined using the received location information of the patient or group of patients, in combination with the physiologic information received from the patient or physiologic information received from a group of patients, such as at an assessment circuit or one or more other medical devices, such as an external programmer configured to communicate with multiple AMDs or to receive information from multiple AMDs associated with multiple patients. In certain examples, an external programmer can be configured to receive pneumonia scores and location information from a number of patients, and can be configured to determine geographic indicators of pneumonia or pneumonia related events using the received pneumonia scores and location information. If any physical locations illustrate rates of events above a threshold, or an increase in event rate above a threshold, such as with respect to other physical locations, medical system capacity, etc., an alert can be provided. Further, indications of worsening pneumonia status can be determined early, before hospitalization is required. Early intervention may reduce the severity of impact to individual patients and to medical system capacity.

In certain examples, one or more of steps 602-606 or 608-609 are optional, or can be combined with steps 601 and 607 in various combinations or permutations. In an example, the external programmer may include the assessment circuit configured to receive physiologic information from the patient or group of patients, such that the external programmer can be configured to determine the pneumonia score of the patient or group of patients, such as opposed to one or more AMDs.

Figure 7:
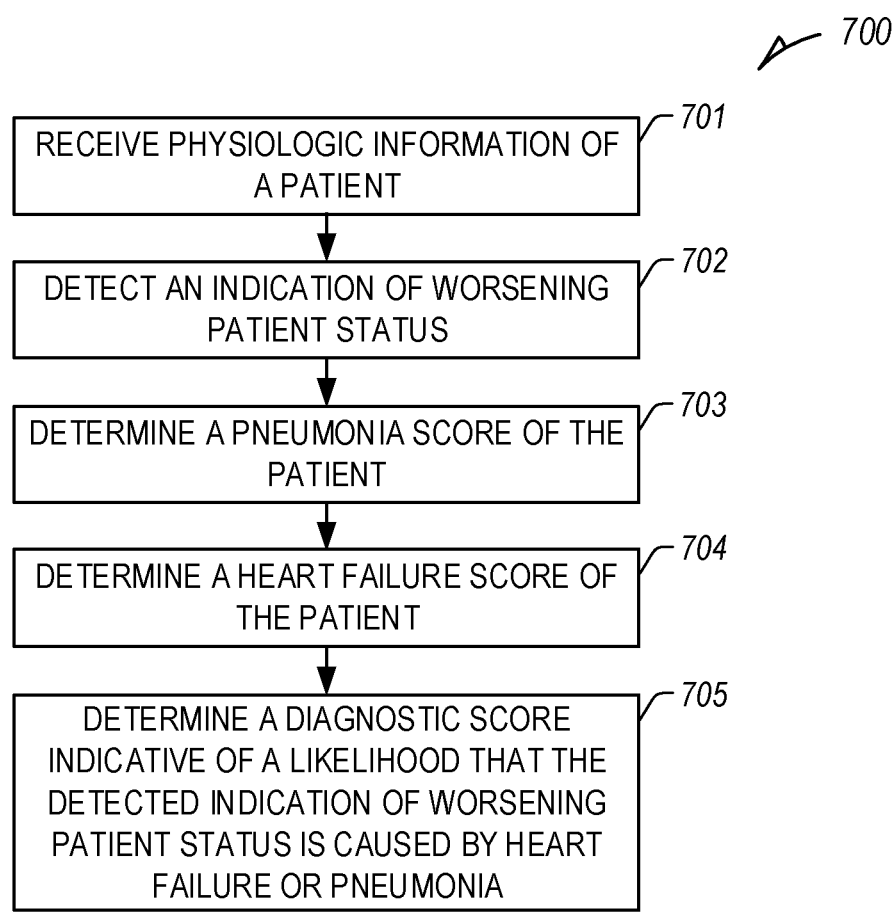
FIG. 7 illustrates an example method to determine a diagnostic score indicative of a likelihood that a detected indication of worsening patient status is caused by heart failure or pneumonia.

FIG. 7 illustrates an example method 700 to determine a diagnostic score indicative of a likelihood that a detected indication of worsening patient status is caused by pneumonia or one or more other acute or chronic cardiac conditions or complications, such as heart failure, etc.

At 701, physiologic information can be received from the patient, such as using a signal receiver circuit of an ambulatory medical device, a medical device programmer, or one or more other implantable, external, ambulatory, or remote medical devices, such as disclosed herein.

At 702, an indication of worsening patient status can be detected, such as using a comparison of the received physiologic information or a change in the received physiologic information over one or more time periods to one or more thresholds. In an example, the indication of worsening patient status can include an indication of worsening heart failure.

At 703, a pneumonia score of the patient can be detected using received physiologic information (e.g., the same or different physiologic information used to detect the indication of worsening patient status), such as otherwise described herein. At 704, a heart failure score of the patient or one or more other cardiac conditions or complications of the patient can be detected using received physiologic information (e.g., the same or different physiologic information used to detect the indication of worsening patient status).

At 705, a diagnostic score indicative of the likelihood that the detected indication of worsening patient status is caused by pneumonia or one or more cardiac conditions or complications different than pneumonia can be determined. For example, the one or more cardiac conditions can include heart failure. The diagnostic score can be a differential diagnostic score indicative of the likelihood that the detected worsening patient status is caused by heart failure or pneumonia using the determined pneumonia score and the determined heart failure score, such as a comparison of the determined pneumonia and heart failure scores, etc.

In other examples, the diagnostic score indicative of the likelihood that the detected indication of worsening patient status is caused by heart failure or pneumonia can include a first indication that the detected indication of worsening patient status is caused by heart failure and a second indication that the detected indication of worsening patient status is caused by pneumonia. In an example, the first and second indications can be determined using a change in determined pneumonia and heart failure scores, a combination of the determined pneumonia and heart failure scores and a history of the patient, etc.

In an example, the detected indication of worsening patient status at 702 can trigger one or more of the determination of pneumonia score of the patient at 703, determination of the heart failure score or other cardiac condition or complication at 704, or determination of the diagnostic score at 705. In other examples, the detected indication of worsening patient status at 702 can trigger detection of or receiving one or more types of physiologic information otherwise not being detected, or scheduled to be detected at the time of such detection, such that operation of one or more AMDs are altered in response to the detected indication. In an example, the determine pneumonia score can be used to alter one or more other scores or alerts, such as existing heart failure scores or alerts.

Figure 8:
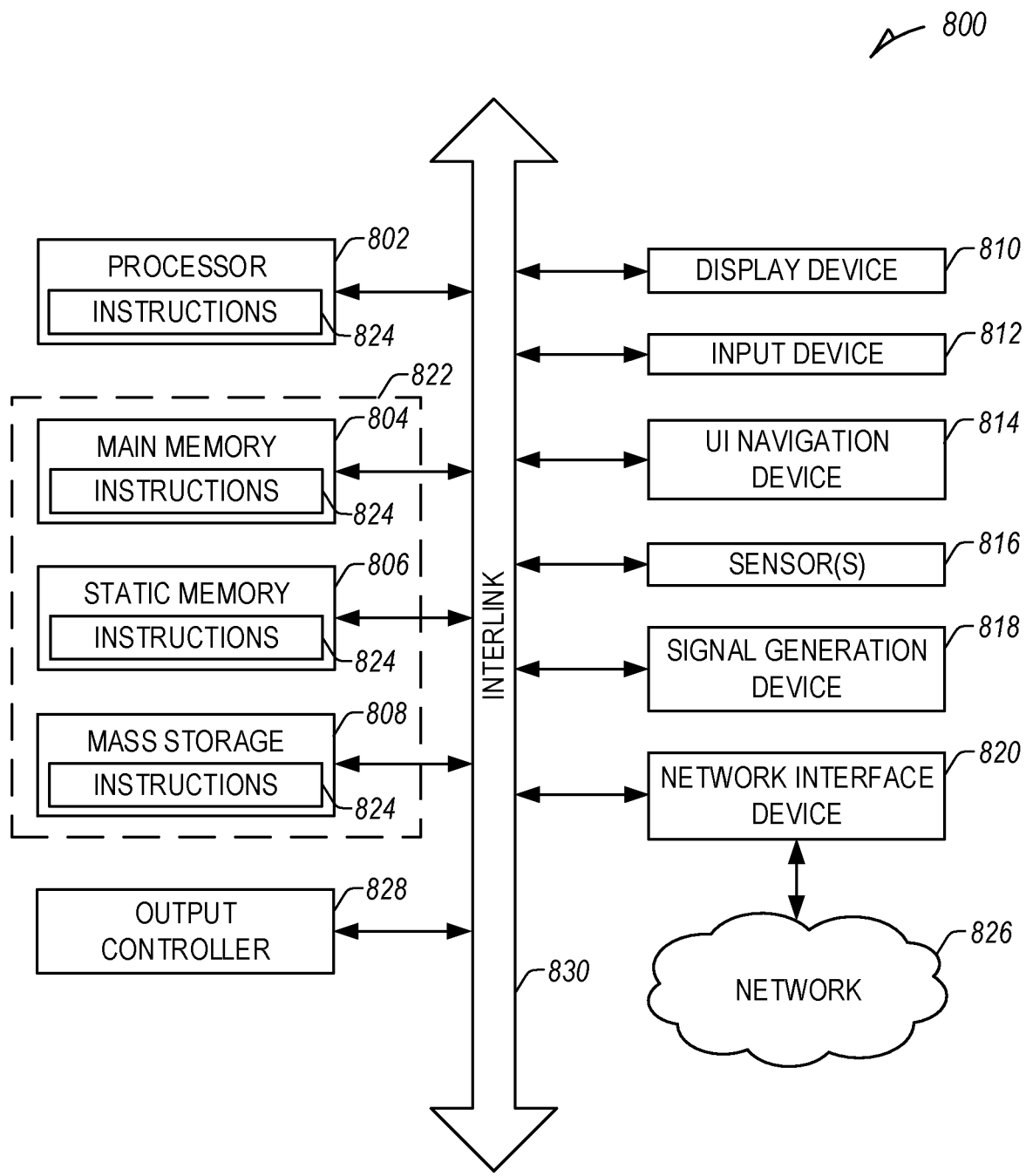
FIG. 8 illustrates a block diagram of an example machine upon which any one or more of the techniques (e.g., methodologies) discussed herein may perform.

FIG. 8 illustrates a block diagram of an example machine 800 upon which any one or more of the techniques (e.g., methodologies) discussed herein may perform. Portions of this description may apply to the computing framework of one or more of the medical devices described herein, such as the IMD, the external programmer, etc. Further, as described herein with respect to medical device components, systems, or machines, such may require regulatory-compliance not capable by generic computers, components, or machinery.

Examples, as described herein, may include, or may operate by, logic or a number of components, or mechanisms in the machine 800. Circuitry (e.g., processing circuitry, an assessment circuit, etc.) is a collection of circuits implemented in tangible entities of the machine 800 that include hardware (e.g., simple circuits, gates, logic, etc.). Circuitry membership may be flexible over time. Circuitries include members that may, alone or in combination, perform specified operations when operating. In an example, hardware of the circuitry may be immutably designed to carry out a specific operation (e.g., hardwired). In an example, the hardware of the circuitry may include variably connected physical components (e.g., execution units, transistors, simple circuits, etc.) including a machine-readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuitry in hardware via the variable connections to carry out portions of the specific operation when in operation. Accordingly, in an example, the machine-readable medium elements are part of the circuitry or are communicatively coupled to the other components of the circuitry when the device is operating. In an example, any of the physical components may be used in more than one member of more than one circuitry. For example, under operation, execution units may be used in a first circuit of a first circuitry at one point in time and reused by a second circuit in the first circuitry, or by a third circuit in a second circuitry at a different time. Additional examples of these components with respect to the machine 800 follow.

In alternative embodiments, the machine 800 may operate as a standalone device or may be connected (e.g., networked) to other machines. In a networked deployment, the machine 800 may operate in the capacity of a server machine, a client machine, or both in server-client network environments. In an example, the machine 800 may act as a peer machine in peer-to-peer (P2P) (or other distributed)

network environment. The machine 800 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

The machine (e.g., computer system) 800 may include a hardware processor 802 (e.g., a central processing unit (CPU), a graphics processing unit (GPU), a hardware processor core, or any combination thereof), a main memory 804, a static memory (e.g., memory or storage for firmware, microcode, a basic-input-output (BIOS), unified extensible firmware interface (UEFI), etc.) 806, and mass storage 808 (e.g., hard drive, tape drive, flash storage, or other block devices) some or all of which may communicate with each other via an interlink (e.g., bus) 830. The machine 800 may further include a display unit 810, an alphanumeric input device 812 (e.g., a keyboard), and a user interface (UI) navigation device 814 (e.g., a mouse). In an example, the display unit 810, input device 812, and UI navigation device 814 may be a touch screen display. The machine 800 may additionally include a signal generation device 818 (e.g., a speaker), a network interface device 820, and one or more sensors 816, such as a global positioning system (GPS) sensor, compass, accelerometer, or one or more other sensors. The machine 800 may include an output controller 828, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

Registers of the processor 802, the main memory 804, the static memory 806, or the mass storage 808 may be, or include, a machine-readable medium 822 on which is stored one or more sets of data structures or instructions 824 (e.g., software) embodying or utilized by any one or more of the techniques or functions described herein. The instructions 824 may also reside, completely or at least partially, within any of registers of the processor 802, the main memory 804, the static memory 806, or the mass storage 808 during execution thereof by the machine 800. In an example, one or any combination of the hardware processor 802, the main memory 804, the static memory 806, or the mass storage 808 may constitute the machine-readable medium 822. While the machine-readable medium 822 is illustrated as a single medium, the term "machine-readable medium" may include a single medium or multiple media (e.g., a centralized or distributed database, and/or associated caches and servers) configured to store the one or more instructions 824.

The term "machine-readable medium" may include any medium that is capable of storing, encoding, or carrying instructions for execution by the machine 800 and that cause the machine 800 to perform any one or more of the techniques of the present disclosure, or that is capable of storing, encoding, or carrying data structures used by or associated with such instructions. Non-limiting machine-readable medium examples may include solid-state memories, optical media, magnetic media, and signals (e.g., radio frequency signals, other photon-based signals, sound signals, etc.). In an example, a non-transitory machine-readable medium comprises a machine-readable medium with a plurality of particles having invariant (e.g., rest) mass, and thus are compositions of matter. Accordingly, non-transitory machine-readable media are machine-readable media that do not include transitory propagating signals. Specific examples of non-transitory machine-readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 824 may be further transmitted or received over a communications network 826 using a transmission medium via the network interface device 820 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.12 family of standards known as Wi-Fi®, IEEE 802.16 family of standards known as WiMax®), IEEE 802.15.4 family of standards, peer-to-peer (P2P) networks, among others. In an example, the network interface device 820 may include one or more physical jacks (e.g., Ethernet, coaxial, or phone jacks) or one or more antennas to connect to the communications network 826. In an example, the network interface device 820 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding, or carrying instructions for execution by the machine 800, and includes digital or analog communications signals or other intangible medium to facilitate communication of such software. A transmission medium is a machine-readable medium.

Various embodiments are illustrated in the figures above. One or more features from one or more of these embodiments may be combined to form other embodiments. Method examples described herein can be machine or computer-implemented at least in part. Some examples may include a computer-readable medium or machine-readable medium encoded with instructions operable to configure an electronic device or system to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A medical system, comprising:
a signal receiver circuit configured to receive physiologic information of a patient from an ambulatory medical device (AMD), the physiologic information comprising respiration information of the patient; and
an assessment circuit configured to determine a pneumonia score of the patient indicative of a prediction of a future adverse pneumonia event within a time period using changes in daily respiration information of the patient over multiple days, wherein the changes in daily respiration information are determined using the received respiration information.

2. The medical system of claim 1, wherein the respiration information of the patient comprises respiratory rate information and respiratory volume information of the patient, and
wherein the assessment circuit is configured to determine a rapid shallow breathing index (RSBI) value for the patient with respect to a first time period using the received respiration information, and to determine the pneumonia score of the patient using the determined RSBI value for the patient with respect to the first time period.

3. The medical system of claim 2, wherein the first time period is a daily time period and the RSBI value for the patient with respect to the first time period comprises a daily RSBI value for the patient, and
wherein the assessment circuit is configured to determine a change in the daily RSBI value for the patient over multiple days, and to determine the pneumonia score of the patient using the determined change in the daily RSBI value.

4. The medical system of claim 1, wherein the physiologic information comprises heart rate information of the patient, and
wherein the assessment circuit is configured to determine the pneumonia score of the patient using the received respiration information and the received heart rate information.

5. The medical system of claim 1, wherein the physiologic information comprises respiration information of the patient, heart sound information of the patient, and activity information of the patient,
wherein the respiration information comprises respiratory rate information of the patient,
wherein the heart sound information comprises third heart sound (S3) information of the patient,
wherein the activity information comprises an indication of daily activity above an activity threshold of the patient, and
wherein the assessment circuit is configured to determine the pneumonia score of the patient using a combination of the received respiratory rate information of the patient, the received third heart sound (S3) information of the patient, and the received indication of daily activity above the activity threshold of the patient.

6. The medical system of claim 1, wherein the physiologic information comprises temperature information of the patient,
wherein the assessment circuit is configured to determine the pneumonia score of the patient using the received respiration information and the received temperature information of the patient, and
wherein, to determine the pneumonia score of the patient, the assessment circuit is configured to determine at least one of an indication of worsening pneumonia status or a prediction of a future pneumonia event of the patient,
wherein the future pneumonia event includes hospitalization with a diagnosis of pneumonia.

7. The medical system of claim 1, wherein the physiologic information comprises respiration information of the patient, heart sound information of the patient, and activity information of the patient, and
wherein the assessment circuit is configured to:
detect an indication of worsening patient status using the received physiologic information of the patient;
determine a heart failure score of the patient using a combination of the received respiration information of the patient, the received heart sound information of the patient, and the received activity information of the patient; and
determine a diagnostic score indicative of a likelihood that the detected indication of worsening patient status is caused by heart failure or pneumonia using the determined pneumonia score and the determined heart failure score.

8. The medical system of claim 7, wherein the diagnostic score indicative of the likelihood that the detected indication of worsening patient status is caused by heart failure or pneumonia comprises a first indication that the detected indication of worsening patient status is caused by heart failure and a second indication that the detected indication of worsening patient status is caused by pneumonia.

9. The medical system of claim 1, comprising an external programmer configured to receive physiologic information from each of a group of patients, wherein the external programmer is configured to receive location information from each of the group of patients, and to determine geographic indicators of pneumonia related events of the group of patients using the received physiologic information and the receive location information.

10. The medical system of claim 9, wherein the external programmer includes the assessment circuit, and
wherein the external programmer is configured to determine the geographic indicators of pneumonia related events of the group of patients using the determined pneumonia score and the received location information for each of the group of patients.

11. A method, comprising:
receiving, at a signal receiver circuit, physiologic information of a patient from an ambulatory medical device (AMD), the physiologic information comprising respiration information of the patient; and
determining, using an assessment circuit, a pneumonia score of the patient indicative of a prediction of a future adverse pneumonia event within a time period using changes in daily respiration information of the patient over multiple days, wherein the changes in daily respiration information are determined using the received respiration information.

12. The method of claim 11, wherein the respiration information of the patient comprises respiratory rate information and respiratory volume information of the patient, the method comprising:
determining, using the assessment circuit, a rapid shallow breathing index (RSBI) value for the patient with respect to a first time period using the received respiration information,
wherein determining the pneumonia score of the patient comprises using the determined RSBI value for the patient with respect to the first time period.

13. The method of claim 12, wherein the first time period is a daily time period and the RSBI value for the patient with respect to the first time period comprises a daily RSBI value for the patient, the method comprising:
  determining, using the assessment circuit, a change in the daily RSBI value for the patient over multiple days,
  wherein determining the pneumonia score of the patient comprises using the determined change in the daily RSBI value.

14. The method of claim 11, wherein the physiologic information comprises heart rate information of the patient, and
  wherein determining the pneumonia score of the patient comprises using the received respiration information and the received heart rate information.

15. The method of claim 11, wherein the physiologic information comprises respiration information of the patient, heart sound information of the patient, and activity information of the patient,
  wherein the respiration information comprises respiratory rate information of the patient,
  wherein the heart sound information comprises third heart sound (S3) information of the patient,
  wherein the activity information comprises an indication of daily activity above an activity threshold of the patient,
  wherein determining the pneumonia score of the patient comprises using a combination of the received respiratory rate information of the patient, the received third heart sound (S3) information of the patient, and the received indication of daily activity above the activity threshold of the patient.

16. The method of claim 11, wherein the physiologic information comprises respiration information of the patient, heart sound information of the patient, and activity information of the patient, the method comprising:
  detecting, using the assessment circuit, an indication of worsening patient status using the received physiologic information of the patient;
  determining, using the assessment circuit, a heart failure score of the patient using a combination of the received respiration information of the patient, the received heart sound information of the patient, and the received activity information of the patient; and
  determining, using the assessment circuit, a diagnostic score indicative of a likelihood that the detected indication of worsening patient status is caused by heart failure or pneumonia using the determined pneumonia score and the determined heart failure score.

17. The method of claim 16, wherein determining the diagnostic score indicative of the likelihood that the detected indication of worsening patient status is caused by heart failure or pneumonia comprises:
  determining a first indication that the detected indication of worsening patient status is caused by heart failure; and
  determining a second indication that the detected indication of worsening patient status is caused by pneumonia.

18. The method of claim 11, comprising:
  receiving, using an external programmer, physiologic information from each of a group of patients and location information from each of the group of patients; and
  determining, using the external programmer, geographic indicators of pneumonia related events of the group of patients using the received physiologic information and the receive location information.

19. At least one machine-readable medium comprising instructions that, when performed by a medical device, cause the medical device to:
  receive physiologic information of a patient from an ambulatory medical device (AMD), the physiologic information comprising respiration information of the patient; and
  determine a pneumonia score of the patient indicative of a prediction of a future adverse pneumonia event within a time period using changes in daily respiration information of the patient over multiple days, wherein the changes in daily respiration information are determined using the received respiration information.

20. The at least one machine-readable medium of claim 19, wherein the instructions, when performed by the medical device, cause the medical device to:
  determine a rapid shallow breathing index (RSBI) value for the patient with respect to a daily time period of the patient using the received respiration information; and
  determine a change in the daily RSBI value for the patient over multiple days,
  wherein to determine the pneumonia score of the patient comprises using the determined change in the daily RSBI value.

* * * * *